(12) United States Patent
Schmidt et al.

(10) Patent No.: US 8,357,695 B2
(45) Date of Patent: Jan. 22, 2013

(54) HYDRATES OF 2-CHLORO-5-[3,6-DIHYDRO-3-METHYL-2,6-DIOXO-4-(TRIFLUOROMETHYL)-1-(2H)-PYRIMIDINYL]-4-FLUORO-N-[[METHYL(1-METHYLETHYL)AMINO]SULFONYL]BENZAMIDE

(75) Inventors: Thomas Schmidt, Neustadt (DE); Joachim Gebhardt, Wachenheim (DE); Sandra Löhr, Ludwigshafen (DE); Michael Keil, Freinsheim (DE); Jan Hendrik Wevers, Hohen-Sülzen (DE); Peter Erk, Frankenthal (DE); Heidi Emilia Saxell, Carlsberg (DE); Gerhard Hamprecht, Weinheim (DE); Guido Mayer, Gönnheim (DE); Bernd Wolf, Fußgönheim (DE); Gerhard Cox, Bad Dükheiim (DE); Alfred Michel, Ramsen (DE); Werner Seitz, Plankstadt (DE); Cyrill Zagar, Hong Kong (CN); Robert Reinhard, Limburgerhof (DE); Bernd Sievernich, Haβloch (DE)

(73) Assignee: BASF SE, Ludwigshafen (DE)

( * ) Notice: Subject to any disclaimer, the term of this patent is extended or adjusted under 35 U.S.C. 154(b) by 426 days.

(21) Appl. No.: 12/444,651

(22) PCT Filed: Oct. 12, 2007

(86) PCT No.: PCT/EP2007/060880
§ 371 (c)(1),
(2), (4) Date: Apr. 7, 2009

(87) PCT Pub. No.: WO2008/043836
PCT Pub. Date: Apr. 17, 2008

(65) Prior Publication Data
US 2010/0035905 A1    Feb. 11, 2010

(30) Foreign Application Priority Data
Oct. 13, 2006   (EP) .................... 06122264

(51) Int. Cl.
*A01N 43/54*  (2006.01)
*A61K 31/505*  (2006.01)

(52) U.S. Cl. ...................... 514/274; 544/312

(58) Field of Classification Search ............ 544/311, 544/312
See application file for complete search history.

(56) References Cited

U.S. PATENT DOCUMENTS

| 4,885,027 A * | 12/1989 | Pomidor ............ 504/333 |
| 7,232,926 B2 * | 6/2007 | Hamprecht et al. ........ 562/822 |
| 2004/0249164 A1 * | 12/2004 | Bratz et al. ............ 546/316 |
| 2005/0159622 A1 | 7/2005 | Hamprecht et al. |
| 2006/0293520 A1 * | 12/2006 | Hamprecht et al. ........ 544/309 |
| 2008/0033174 A1 | 2/2008 | Lohr et al. |
| 2008/0293941 A1 | 11/2008 | Gebhardt et al. |

FOREIGN PATENT DOCUMENTS

| WO | WO 01/83459 | 11/2001 |
| WO | WO 0183459 A2 * | 11/2001 |
| WO | WO 03/097589 | 11/2003 |
| WO | WO 2005/054208 | 6/2005 |
| WO | WO 2006/010474 | 2/2006 |
| WO | WO 2006/125746 | 11/2006 |
| WO | WO 2008/043835 | 4/2008 |

OTHER PUBLICATIONS

S.L. Morissette et al., Advanced Drug Delivery Reviews, 56, 275-300 (2004).*
R.K. Khankari et al., Thermochimica Acta, 248, 6179 (1995).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
S.R. Byrn et al, Solid-State Chemistry of Drugs, 516 (2nd ed., 1999).*
International Search Report completed Dec. 6, 2007 International Application No. PCT/EP2007/060880, filed Oct. 12, 2007.
English language translation of the International Preliminary Report on Patentability from corresponding International Application No. PCT/EP2007/060880, filed Oct. 12, 2007.

* cited by examiner

*Primary Examiner* — James O Wilson
*Assistant Examiner* — Alexander R Pagano
(74) *Attorney, Agent, or Firm* — Brinks Hofer Gilson & Lione

(57) ABSTRACT

The present invention relates to hydrates of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]-sulfonyl]benzamide. The invention also relates to a process for the preparation of these hydrates and to plant protection formulations which comprise hydrates of the phenyluracil I.

15 Claims, 4 Drawing Sheets

Figure 1:
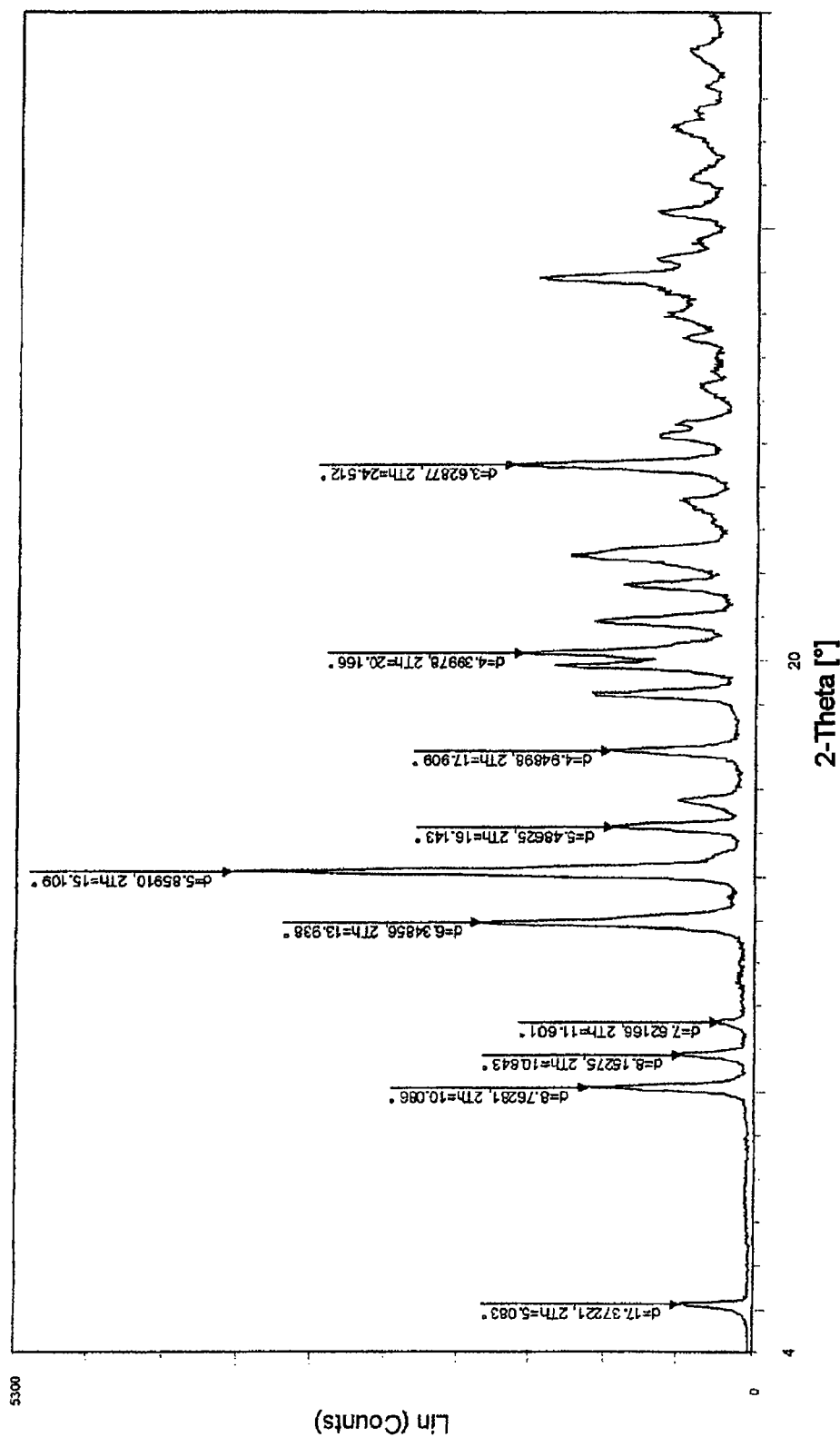

HYDRATES OF 2-CHLORO-5-[3,6-DIHYDRO-3-METHYL-2,6-DIOXO-4-(TRIFLUOROMETHYL)-1-(2H)-PYRIMIDINYL]-4-FLUORO-N-[[METHYL(1-METHYLETHYL)AMINO]SULFONYL]BENZAMIDE

This application is a National Stage application of International Application No. PCT/EP2007/060880 filed Oct. 12, 2007. This application also claims the benefit under 35 U.S.C. §119 of European Patent Application No. 06122264.2, filed Oct. 13, 2006.

The present invention relates to hydrates of 2-chloro-5-[3,6-dihydro-3-methyl-2,6-dioxo-4-(trifluoromethyl)-1-(2H) pyrimidinyl]-4-fluoro-N-[[methyl(1-methylethyl)amino]-sulfonyl]benzamide, hereinbelow also referred to a phenyluracil I. The invention also relates to a process for the preparation of these hydrates and to crop protection formulations which comprise hydrates of the phenyluracil I.

The phenyluracil I, which has the following formula:

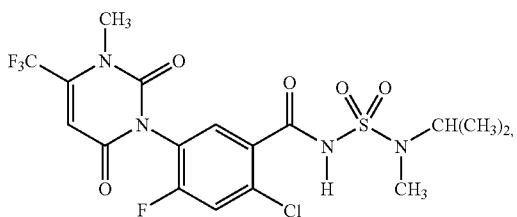

is a herbicidal active substance which is disclosed in WO 01/083459. Further processes for its preparation are disclosed in WO 03/097589, WO 05/054208 and WO 06/097589 and the earlier international application PCT/EP 2006/062414. All known processes for preparing phenyluracil I provide it as an amorphous substance.

Studies undertaken by the assignee company have demonstrated that the amorphous phenyluracil I is only moderately suitable for the preparation of formulations which comprise the substance as solid. Stability problems may occur in particular in the case of multi-phase formulations.

Surprisingly, it has now been found that suitable processes give hydrates of the phenyluracil I which do not have these disadvantages. Moreover, it has, surprisingly, emerged that these hydrates have a better herbicidal activity and, in a series of crops, have better crop plant tolerance, than the amorphous form of the phenyluracil I known to date. The hydrates of the phenyluracil I are crystalline substances which are more compact than the amorphous form known to date. The hydrates can therefore be handled with greater ease than the amorphous form of the phenyluracil I which is known to date.

Accordingly, the present invention relates to hydrates of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide.

The hydrates of the phenyluracil I are crystalline substances which, depending on the form of the crystallites, comprise approximately 0.8 to 1.2 mol of water, in particular 0.9 to 1.1 mol and specifically 0.95 to 1.05 mol water per mole of phenyluracil, and which can therefore be considered monohydrates. The composition can be determined by determining the amount of water by the Karl Fischer method.

The hydrates melt in a temperature range of from 100 to 150° C., depending on the heating rate and the type of sample container. In open sample containers and at low heating rates of up to 2 K/min, the hydrates melt in the range of from 100 to 130° C., whereas the melting range is shifted towards higher values when the heating rates are higher and/or when sealed sample containers are used. In sealed sample containers and at heating rates of 5 K/min, the melting range is typically in the range of from 120 to 150° C., with a peak maximum in the range of from 130 to 140° C. The melting points detailed herein refer to values determined by differential scanning calorimetry (DSC, crucible material aluminum).

A more detailed study of the hydrates has revealed that they are generated in two different forms, hereinbelow also referred to as hydrate (a) and hydrate (b), but which are identical with regard to composition and similar with regard to melting points. To differentiate them from the known amorphous form, hereinbelow also referred to as form I, hydrate (a) according to the invention will hereinbelow also be referred to as form III and hydrate (b) according to the invention hereinbelow also as form IV.

Form III according to the invention can be identified by means of X-ray powder diffractometry on the basis of their diffraction diagram. Thus, an X-ray powder diffractogram of form III recorded at 25° C. using Cu—$K_\alpha$ radiation (1.54178 Å) shows at least a characteristic reflex at $2\theta = 11.6 \pm 0.2°$, while form IV shows at least one characteristic reflex at $2\theta = 12.1 \pm 0.2°$.

In particular, an X-ray powder diffractogram of form III shows under these conditions, in addition to the reflex at $2\theta = 11.6 \pm 0.2°$, at least 3, frequently at least 5, in particular at least 7 further, and specifically all of the reflexes detailed in Table 1 hereinbelow as 2θ values, or as interplanar spacings d:

TABLE 1

| 2θ | d [Å] |
|---|---|
| 5.1 ± 0.2° | 17.37 ± 0.02 |
| 10.1 ± 0.2° | 8.76 ± 0.02 |
| 10.8 ± 0.2° | 8.15 ± 0.02 |
| 11.6 ± 0.2° | 7.62 ± 0.02 |
| 13.9 ± 0.2° | 6.35 ± 0.02 |
| 15.1 ± 0.2° | 5.86 ± 0.02 |
| 16.1 ± 0.2° | 5.49 ± 0.02 |
| 17.9 ± 0.2° | 4.95 ± 0.02 |
| 20.2 ± 0.2° | 4.40 ± 0.02 |
| 24.5 ± 0.2° | 3.63 ± 0.02 |

Studies on monocrystals of form III demonstrate that the underlying crystal structure is monoclinic. The unit cell has the space group P2(1)/c. The characteristic data of the crystal structure of form III (determined at −170° C.) are compiled in Table 2.

TABLE 2

| Crystallographic characteristics of form III | |
|---|---|
| Parameter | Form III |
| class | monoclinic |
| space group | P2(1)/c |
| a | 17.624(2) Å |
| b | 9.012(1) Å |
| c | 13.624(1) Å |
| α | 90° |
| β | 92.223(4)° |
| γ | 90° |
| volume | 2162.3(3) Å$^3$ |
| Z | 4 |

TABLE 2-continued

Crystallographic characteristics of form III

| Parameter | Form III |
|---|---|
| density (calculated) | 1.594 Mg/m$^3$ |
| R$^1$; wR$^2$ | 0.096; 0.278 |
| wavelength | 1.54178 Å | a, b, c = unit cell length
α, β, γ = unit cell angle
Z = number of molecules in the unit cell An X-ray powder diffractogram of form IV, which has been recorded at 25° C. using Cu—K$_\alpha$ radiation (1.54178 Å), in turn, shows, as a rule, at least 3, frequently at least 5, in particular at least 7, further and specifically all of the reflexes detailed in Table 3 hereinbelow as 2θ values, or as interplanar spacings d, in addition to the reflex at 2θ=12.03±0.2°.

TABLE 3

| 2θ | d [Å] |
|---|---|
| 5.2 ± 0.2° | 17.21 ± 0.02 |
| 10.2 ± 0.2° | 8.63 ± 0.02 |
| 10.9 ± 0.2° | 8.11 ± 0.02 |
| 12.1 ± 0.2° | 7.32 ± 0.02 |
| 14.0 ± 0.2° | 6.31 ± 0.02 |
| 14.6 ± 0.2° | 6.08 ± 0.02 |
| 15.4 ± 0.2° | 5.77 ± 0.02 |
| 19.2 ± 0.2° | 4.61 ± 0.02 |
| 19.9 ± 0.2° | 4.44 ± 0.02 |
| 20.5 ± 0.2° | 4.33 ± 0.02 |
| 24.7 ± 0.2° | 3.60 ± 0.02 |
| 26.7 ± 0.2° | 3.34 ± 0.02 |
| 27.8 ± 0.2° | 3.21 ± 0.02 |

The hydrates of the phenyluracil I are successfully prepared for example by the processes described hereinbelow, which comprise, as central step, a crystallization from a solution of the phenyluracil I in an organic solvent in the presence of water.

The organic solvents may take the form of those organic solvents which are miscible with water, but also those which have only limited miscibility with water.

Examples of preferred organic solvents, hereinbelow also referred to as solvents L1, are acyclic ethers with 4 to 6 C atoms, such as methyl tert-butyl ether,
alicyclic ethers with 4 to 6 C atoms such as tetrahydrofuran,
dialkyl ketones with 3 to 5 C atoms, in particular acetone,
$C_1$-$C_4$-alkanols such as methanol, ethanol, n-propanol, isopropanol, tert-butanol,
$C_2$-$C_3$-alkylene glycol mono-$C_1$-$C_4$-alkyl ethers such as ethylene glycol methyl ether and ethylene glycol n-propyl ether,
di-($C_2$-$C_3$-alkylene glycol) mono-$C_1$-$C_4$-alkyl ethers,
$C_1$-$C_4$-alkylesters of aliphatic $C_1$-$C_4$-carboxylic acids, in particular $C_1$-$C_4$-alkylesters of acetic acid, such as ethyl acetate and butyl acetate,
aliphatic and aromatic hydrocarbons, in particular mono- and di-$C_1$-$C_4$-alkylbenzenes such as toluene and xylene, and $C_5$-$C_8$-alkanes such as pentane, heptane and hexane,
aliphatic and aromatic chlorohydrocarbons such as dichloromethane and chlorobenzene, and
mixtures of these solvents.

Especially preferred organic solvents are methanol and mono- and di-$C_1$-$C_4$-alkylbenzenes, in particular toluene, and mixtures of mono- and di-$C_1$-$C_4$-alkylbenzenes, in particular toluene, with the abovementioned solvents L1, in particular with tetrahydrofuran and/or with methanol. The mono- or di-$C_1$-$C_4$-alkylbenzene amounts to at least 50% by volume, and in particular at least 80% by volume, in these mixtures, based on the total amount of organic solvent L1.

Besides the abovementioned solvents L1, the organic solvent employed for the crystallization may also comprise other, different organic solvents (hereinbelow solvents L2). As a rule, the amount of the solvent L2 is not more than 50% by volume, in particular not more than 20% by volume, based on the total amount of the organic solvent employed for the crystallization.

In accordance with the invention, the crystallization of the hydrates is accomplished in the presence of water. The latter is, as a rule, added to a solution of the phenyluracil in the organic solvent. In the case of solvents which are capable of dissolving water at least in part, the added water reduces the solubility of the phenyluracil in the organic solvent, and crystallization of the hydrate takes place. In the case of solvents which form a multiphase system with the added amount of water, the crystallization is, as a rule, brought about by cooling.

The amount of water is typically in the range of from 5 to 300 parts by volume, in particular in the range of from 5 to 200 parts by volume, based on 100 parts by volume of organic solvent.

To crystallize the hydrates, a procedure will frequently be followed in which a solution of the phenyluracil I in one of the abovementioned organic solvents is provided and the desired amount of water is added thereto.

The addition of the water can be accomplished at room temperature or at elevated temperature and is typically accomplished at temperatures from 20° C. to the boiling point of the organic solvent employed, but preferably at temperatures of up to a maximum of 90° C. The desired amount of water can be added in one or more portions over a brief period, i.e. up to 10 minutes, or slowly, for example over a period of at least 30 minutes or at least 60 minutes, for example 30 to 300 minutes or 60 to 300 minutes or 120 to 300 minutes.

If the addition of water is accomplished at elevated temperature, the temperature will, as a rule, be lowered after the water has been added. For example, a procedure can be followed in which water is added to the hot solution until crystallization starts, and the mixture is subsequently cooled and, if appropriate, more water is added to complete the crystallization process.

It is also possible to dissolve the phenyluracil I, preferably the amorphous form, in a suitable mixture of organic solvent and water, if appropriate with heating, for example to temperatures in the range of from 40 to 90° C., and to bring about the crystallization by adding more water and/or by cooling.

Processes which are suitable for crystallizing the form III are, for example, those which bring about slow crystallization, for example by adding the water over a prolonged period and/or slowly cooling the mixture of solvent and water and dissolved phenyluracil I.

The formation of form IV, in turn, can be promoted by those measures which bring about rapid crystallization, for example the rapid addition of water or performing the crystallization at temperatures of below 40° C.

The crystallization of form III or IV can be controlled or accelerated by seeding with seed crystals of the respective form, for example by adding seed crystals of the respective form before or during the crystallization process.

In the event that seed crystals are added during the crystallization process, they typically amount to 0.001 to 10% by weight, frequently 0.005 to 5% by weight, in particular 0.01 to 1% by weight and specifically 0.05 to 0.5% by weight, based on the dissolved phenyluracil I.

In the event that the crystallization is carried out in the presence of seed crystals, these are preferably only added at a temperature at which the saturation concentration of the phenyluracil I in the respective solvent has been attained, i.e. at, or below, the temperature at which the dissolved amount of phenyluracil I in the solvent in question forms a saturated solution. The temperature dependence of the saturation concentration in a solvent can be determined by the skilled worker in routine experiments. Frequently, the seed crystals are added when the temperature of the solution is not more than 60° C. Preferably, the mixture is left to cool to temperatures of below 30° C., in particular of 25° C. or less, for example to temperatures in the range of from 0° C. to 25° C., after addition of the seed crystals, before the resulting crystalline material is isolated from the mother liquor in order to isolate the hydrate of the phenyluracil I. Cooling in the presence of seed crystals can be performed in a controlled fashion at a cooling rate of, as a rule, not more than 30 K/h, for example 1 to 30 K/h, frequently 2 to 20 K/h and in particular 3 to 15 K/h, or in a noncontrolled fashion.

After the addition of the water, or after cooling has ended, it may be advantageous to suspend the resulting precipitate for some time in the mother liquor, for example over a period of 30 minutes to 3 days, before the crystallizate is isolated from the mother liquor.

As an alternative, it is also possible to suspend the phenyluracil I, preferably the amorphous form, in water or a mixture of water and an organic solvent, during which process an inventive hydrate of the phenyluracil I forms after some time. The last-mentioned route is particularly suitable for the preparation of form IV. As regards the organic solvents, what has been said above also applies here analogously.

Obtaining the hydrates from the crystallization mixture, i.e. the isolation of the hydrate from the mother liquor, is accomplished by customary techniques for separating solid constituents from liquids, for example by filtration, centrifuging or by decanting. As a rule, the isolated solid will be washed, for example with the solvent used for the crystallization, with water or with a mixture of the organic solvents used for the crystallization and water. Washing can be accomplished in one or more steps, the last wash step frequently being carried out with water. Washing is typically accomplished at temperatures below 30° C., frequently below 25° C. and in particular below 20° C., in order to keep the losses of product of interest as low as possible. Thereafter, the resulting hydrate may be dried carefully in order to avoid the loss of hydrate water, and then further processed. Frequently, however, the moist active substance obtained after washing, in particular an aqueous-moist active substance, will be further processed directly.

The crystallization according to the invention yields a phenyluracil I which consists essentially of a hydrate according to the invention, i.e. the amount of hydrate based on the total amount of phenyluracil I in the crystallization mixture is typically at least 90%, frequently at least 95% and in particular at least 98%. The purity of the phenyluracil in the hydrates obtained, i.e. the amount of phenyluracil I, based on the total amount of the organic constituents present in the hydrate, is, as a rule, at least 94% by weight, in particular at least 96% by weight.

The solution employed for the crystallization of the phenyluracil I can be provided for example by the following methods:

(1) dissolving the phenyluracil I, preferably in a form which differs from the hydrates, in an organic solvent or solvent/water mixture; or (2) preparation of the phenyluracil I by chemical reaction and transfer of the reaction mixture, if appropriate after removal of reagents and/or by-products, into an organic solvent which is suitable in accordance with the invention.

In principle, any known form of the phenyluracil I may be employed for preparing the solution by dissolving the phenyluracil I. Naturally, a form of the phenyluracil I which differs from the hydrate forms will be used. Suitable for this purpose are in particular a solid or liquid melt of the phenyluracil or amorphous phenyluracil I as known from the prior art. In addition to the amorphous form I of the phenyluracil, the crystalline anhydrate form II of the phenyluracil is also suitable. The anhydrate form II is the subject matter of a parallel patent application which is referred to herewith in its entirety.

The solvent used for dissolving the phenyluracil I typically takes the form of one of the abovementioned organic solvents L1 or a mixture of different solvents L1 or a solvent mixture which comprises at least 70% by weight and specifically at least 90% by weight of solvent L1, based on the total amount of solvent employed for the purpose of dissolving.

To dissolve the form of the phenyluracil I which differs from the hydrate forms III and IV, the phenyluracil I will usually be incorporated into the solvent in the form of finely particulate solid or as a melt commixing, which process is carried out at a temperature at which the solvent, or solvent mixture, is capable of fully dissolving the phenyluracil I.

Dissolving the phenyluracil I is usually performed at temperatures in the range of from 20 to 160° C. In a preferred embodiment of the invention, dissolving of the phenyluracil I takes place at elevated temperature, in particular at least 50° C., specifically at least 80° C., where, naturally, the temperature employed for dissolving will not exceed the boiling point of the solvent. Frequently, the dissolving is carried out at temperatures in the range of from 50 to 140° C., in particular in the range of from 80 to 120° C. and especially preferably in the range of from 95 to 115° C.

The amount of phenyluracil I which is dissolved in the solvent will naturally depend on the nature of the solvent L1 and the dissolving temperature, and is frequently in the range of from 50 to 800 g/l. Suitable conditions can be determined by the skilled worker by routine experiments.

The solution of the phenyluracil I can also be provided by transferring a reaction mixture which has been obtained as the result of a chemical reaction and which comprises the phenyluracil I into an organic solvent or solvent/water mixture which is suitable in accordance with the invention, if appropriate after having removed reagents and/or by-products. Here, a procedure may be followed in which the reaction is carried out in an organic solvent or solvent mixture which is composed at least in part, preferably to at least 50% by weight, of a solvent which is suitable for the crystallization and, if appropriate, a work-up is performed, where excess reagents and any catalysts which may be present and any unsuitable solvent which may be present are removed. The preparation of a solution of the phenyluracil I by chemical reaction of a suitable precursor of the phenyluracil I, can be performed in analogy to the methods which are described in the prior art cited at the outset, which is herewith referred to in its entirety.

The preparation of the hydrates III and IV may also be accomplished departing from amorphous 2-chloro-5-[3,6-dihydro-3-methyl-2,6-dioxo-4-(trifluoromethyl)-1-(2H)-pyrimidinyl]-4-fluoro-N-[[methyl(1-methylethyl)amino]sulfonyl]benzamide by suspending the amorphous phenyluracil in water or a water-containing organic solvent. Suitable organic solvents are in particular those solvents L1 which are capable of dissolving at least 100 g/l water at 298 K and 1 bar. These include, in particular, dialkyl ketones with 3 to 5 C atoms, $C_1$-$C_4$-alkanols, $C_2$-$C_3$-alkylene glycol mono-$C_1$-$C_4$-alkyl ethers, di-($C_2$-$C_3$-alkylene glycol)mono-$C_1$-$C_4$-alkyl ethers, tetrahydrofuran and mixtures of these solvents. If a mixture of water and organic solvent is employed, the amount of water is typically 50 to 2000 parts by volume, based on 100 parts by volume of organic solvent.

The preparation of the 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide employed as a starting material for the preparation of the hydrates can be accomplished by the methods described in WO 01/083459, WO 03/097589, WO 05/054208, WO 06/097589 and PCT/EP 2006/062414, which are hereby incorporated herein in their entirety by reference.

It is especially preferred to prepare the phenyluracil I by the following methods:

1) Conversion of 2-chloro-5-[3,6-dihydro-2,6-dioxo-4-(trifluoromethyl)-1(2H)-pyrimidinyl]-4-fluorobenzoic acid into its acid chloride or the corresponding anhydride and subsequent conversion of the corresponding activated acid derivative with N-methyl-N-(1-methylethyl)sulfamoylamide, for example:

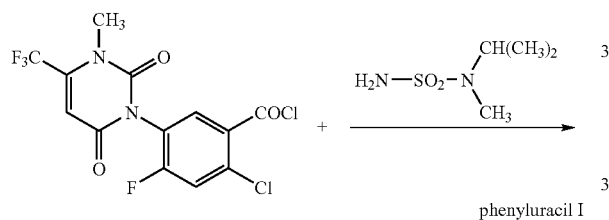

phenyluracil I

This reaction is usually carried out at temperatures of from 20° C. to the boiling point of the reaction mixture in an organic solvent in the presence of a base and, if appropriate, of a catalyst [cf., for example, WO 01/083459, WO 03/097589 and also WO 04/039768].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide. Mixtures of the abovementioned solvents may also be employed.

Bases which are suitable are, generally, inorganic bases such as alkali metal and alkaline-earth metal hydroxides such as lithium hydroxide, sodium hydroxide, potassium hydroxide and calcium hydroxide, alkali metal and alkaline-earth metal oxides such as lithium oxide, sodium oxide, calcium oxide and magnesium oxide, alkali metal and alkaline-earth metal hydrides such as lithium hydride, sodium hydride, potassium hydride and calcium hydride, alkali metal amides such as lithium amide, sodium amide and potassium amide, alkali metal and alkaline-earth metal carbonates such as lithium carbonate, potassium carbonate and calcium carbonate and also alkali metal bicarbonates such as sodium bicarbonate, organometallic compounds, in particular alkali metal alkyls such as methyllithium, butyllithium and phenyllithium, alkyl magnesium halides such as methyl magnesium chloride and alkali metal and alkaline-earth metal alkoxides such as sodium methoxide, sodium ethoxide, potassium ethoxide, potassium tert-butoxide, potassium tert-pentoxide and dimethoxymagnesium, furthermore organic bases, for example tertiary amines such as trimethylamine, triethylamine, diisopropylethylamine and N-methylpiperidine, pyridine, substituted pyridines such as collidine, lutidine and 4-dimethylaminopyridine, and bicyclic amines.

The bases are generally employed in catalytic or equimolar amounts, but they may also be used in an excess or, if appropriate, as solvents.

The starting materials are generally reacted with each other in equimolar amounts. It may be advantageous to employ one of the starting materials in an excess.

2) Methylation of 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide (hereinbelow "NH-uracil") with a methylating agent C:

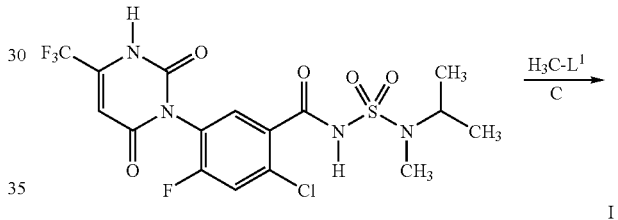

The group $L^1$ represents a nucleophilic leaving group, preferably halogens such as chlorine, bromine or iodine, $C_1$-$C_6$-alkyl sulfate such as methyl sulfate, $C_1$-$C_6$-alkyl-sulfonyloxy such as methylsulfonyloxy, $C_1$-$C_6$-haloalkylsulfonyloxy such as trifluoromethylsulfonyloxy or phenylsulfonyloxy; very preferably $C_1$-$C_6$-alkyl sulfate.

Suitable methylating agents C are methyl halides such as methyl iodide, methyl bromide, methyl chloride, dimethyl sulfate, methyl $C_1$-$C_6$-haloalkylsulfonate, or methyl phenylsulfonate, with methyl halides and dimethyl sulfate being especially preferred; dimethyl sulfate is extraordinarily preferred.

The methylating agent C can be employed either in an equimolar amount based on the NH-uracil, but also in a substoichiometric amount or in an excess.

Process (2) is usually carried out in the presence of a base, with all customary organic and inorganic bases being suitable, for example the bases mentioned in process (1). Preferred bases are selected among alkali metal and alkaline-earth metal hydroxides such as lithium hydroxide, sodium hydroxide, potassium hydroxide and calcium hydroxide, alkali metal and alkaline-earth metal oxides such as lithium oxide, sodium oxide, calcium oxide and magnesium oxide, alkali metal and alkaline-earth metal carbonates such as lithium carbonate, sodium carbonate, potassium carbonate and calcium carbonate and also alkali metal bicarbonates such as sodium bicarbonate. In an especially preferred embodiment, sodium hydroxide or potassium hydroxide is employed as the base. The bases are generally employed in equimolar amounts based on the NH-uracil, but they may also be used in catalytic amounts, in an excess or, if appropriate, as the solvent.

In a very preferred variant of process (2), the pH is kept in a range of from 1 to 6 during all of the reaction by the continuous or portionwise addition of base. "Portionwise addition of base" means that the addition of the base during the conversion is performed in individual portions, i.e. in at least 2 portions, or in more, up to many, portions, or continuously.

To carry out the reaction, the NH-uracil, the methylating agent C and, if appropriate, the base, may be introduced separately, simultaneously or in succession into the reaction vessel and reacted.

In accordance with a first embodiment of process (2), the conversion of the NH-uracil with the methylating agent C is performed in an organic solvent.

Suitable solvents for these reactions are, depending on the temperature range, aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran, 1,4-dioxane, anisole, glycol ethers such as dimethyl glycol ether, diethyl glycol ether, diethylene glycol dimethyl ether, diethylene glycol diethyl ether, $C_1$-$C_4$-alcohols such as methanol, ethanol, n-propanol, isopropanol, n-butanol, $C_1$-$C_6$-alkyl esters of aliphatic carboxylic acids such as methyl acetate, ethyl acetate or n-butyl acetate; ketones such as acetone, methyl ethyl ketone, methyl isopropyl ketone, methyl isobutyl ketone, butanone, carbonates such as diethyl carbonate and ethylene carbonate, N,N-dialkyl amides such as N,N-dimethylformamide or N,N-dimethyl-acetamide, N-alkyllactams such as N-methylpyrrolidone, sulfoxides such as dimethyl sulfoxide, tetraalkylureas such as tetramethylurea, tetraethylurea, tetrabutylureas, dimethylethyleneurea, dimethylpropyleneurea, or mixtures of these solvents.

Preferred solvents are N,N-dialkylamides such as N,N-dimethylformamide, N-alkyllactams such as N-methylpyrrolidone, ketones such as acetone, aromatic hydrocarbons such as toluene, chlorinated aliphatic and aromatic hydrocarbons such as dichloromethane or chlorobenzene, cyclic ethers such as tetrahydrofuran, $C_1$-$C_6$-alkyl esters of aliphatic carboxylic acids such as ethyl acetate, butyl acetate, or mixtures of these solvents.

The methylation of the NH-uracil is preferably accomplished at temperatures between −5° C. and 100° C. The reaction time can be determined by the skilled worker in a manner known per se by routine methods such as thin-layer chromatography or HPLC.

In another variant of process (2a), the conversion can also be carried out in a multiphase system. This variant is preferred.

As regards methylating agent C, pH, base, temperature and pressure, what has been said above also applies here.

In accordance with a second, preferred embodiment of process (2), the reaction of the NH-uracil with the methylating agent C is carried out in an aqueous-organic multiphase system in the presence of one or more phase transfer catalysts.

Examples of phase transfer catalysts are quaternary ammonium salts, phosphonium salts, crown ethers or polyglycols. Preferred suitable quaternary ammonium salts comprise, for example, tetra($C_1$-$C_{18}$)alkylammonium halides and N-benzyltri($C_1$-$C_{18}$)-alkylammonium halides. Preferred suitable phosphonium salts comprise, for example, $C_1$-$C_{18}$-alkyltriphenylphosphonium chlorides, $C_1$-$C_{18}$-alkyltriphenylphosphonium bromides, $C_1$-$C_{18}$-alkyltriphenylphosphonium acetates, tetra($C_1$-$C_{18}$)alkylphosphonium chlorides or tetra($C_1$-$C_{18}$)alkylphosphonium bromides, tetraphenylphosphonium chloride or tetraphenylphosphonium bromide, benzyltriphenylphosphonium chloride or benzyltriphenylphosphonium bromide. Preferred suitable crown ethers comprise, for example, 18-crown-6, dibenzo-18-crown-6. Preferred suitable polyglycols comprise, for example, diethylene glycol dibutyl ether (=butyldiglyme), tetraethylene glycol dimethyl ether (=tetraglyme), triethylene glycol dimethyl ether (=triglyme), polyglycol dimethyl ether. As a rule, the phase transfer catalyst is employed in an amount of up to 20 mol % based on the NH-uracil.

The multiphase system comprises an aqueous phase and at least one organic liquid phase. In addition, solid phases may also be present.

The aqueous phase is preferably a solution which comprises the base, in particular an aqueous solution of alkali metal or alkaline-earth metals hydroxides (such as lithium hydroxide, sodium hydroxide, potassium hydroxide and calcium hydroxide), alkali metal or alkaline-earth metal carbonates (such as lithium carbonate, sodium carbonate, potassium carbonate and calcium carbonate) or alkali metal bicarbonates (such as sodium bicarbonate) in water. It is especially preferred to use alkali metal or alkaline-earth metal hydroxides, very preferably sodium hydroxide.

The base(s) is/are generally employed in equimolar amounts based on the NH-uracil, but may also be used in catalytic amounts, in an excess or, if appropriate, as the solvent. It is preferred to employ at least one equimolar amount of base, based on the NH-uracil.

Suitable solvents for the organic phase, depending on the temperature range, are aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran (THF) and anisole, $C_1$-$C_6$-alkyl esters of aliphatic carboxylic acids such as methyl acetate, ethyl acetate or n-butyl acetate, or mixtures of these solvents. Preferred solvents for the organic phase are ethyl acetate, n-butyl acetate, chlorobenzene, THF, toluene, or mixtures of these solvents; ethyl acetate, n-butyl acetate, chlorobenzene and THF mixtures, and also toluene and THF mixtures, are very preferred.

Solid phases may occur during the conversion, for example when the NH-uracil, the methylating agent C, the base and/or the phase transfer catalyst are not fully dissolved.

In a preferred embodiment, the multiphase system when used as the aqueous phase consists of aqueous sodium hydroxide solution, and when used as the organic phase it consists of toluene and tetrahydrofuran, or dichloromethane and tetrahydrofuran, chlorobenzene and tetrahydrofuran, or of ethyl acetate or n-butyl acetate.

To carry out the conversion, the NH-uracil, the methylating agent C, the base and, if appropriate, the phase transfer catalyst can be introduced separately, simultaneously or in succession into the reaction vessel and reacted therein.

When using a two-phase system, the phases will, as a rule, be separated before form III or IV are crystallized. It is especially preferred to dry the resulting product by drying methods known to the skilled worker, for example by azeotroping the water off together with part of the organic solvent, before carrying out the crystallization.

The figures and examples which follow are intended to illustrate the invention and are not taken to be limiting.

FIG. 1 shows an X-ray powder diffractogram of form III. The X-ray diffractogram of form III was recorded with a diffractometer type D-5000 from Bruker-AXS in reflection geometry in the range of $2\theta=4°-35°$ with a step width of $0.02°$ using the Cu—$K_\alpha$ radiation at 25° C. The reported interplanar spacings d were calculated from the determined $2\theta$ values.

Figure 2:
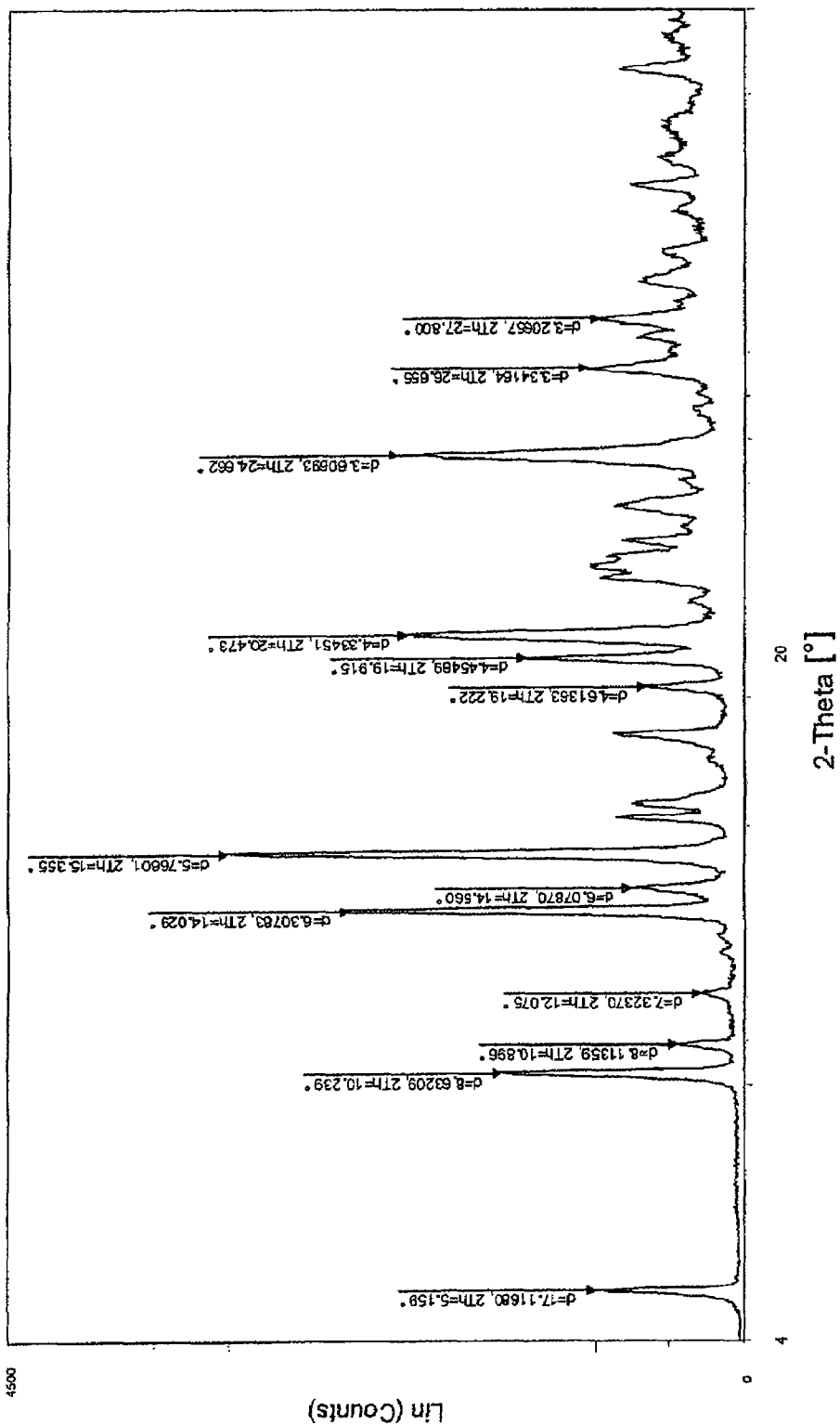

FIG. 2 shows an X-ray powder diffractogram of form IV. As regards the measuring conditions, what has been said above also applies here.

Figure 3:
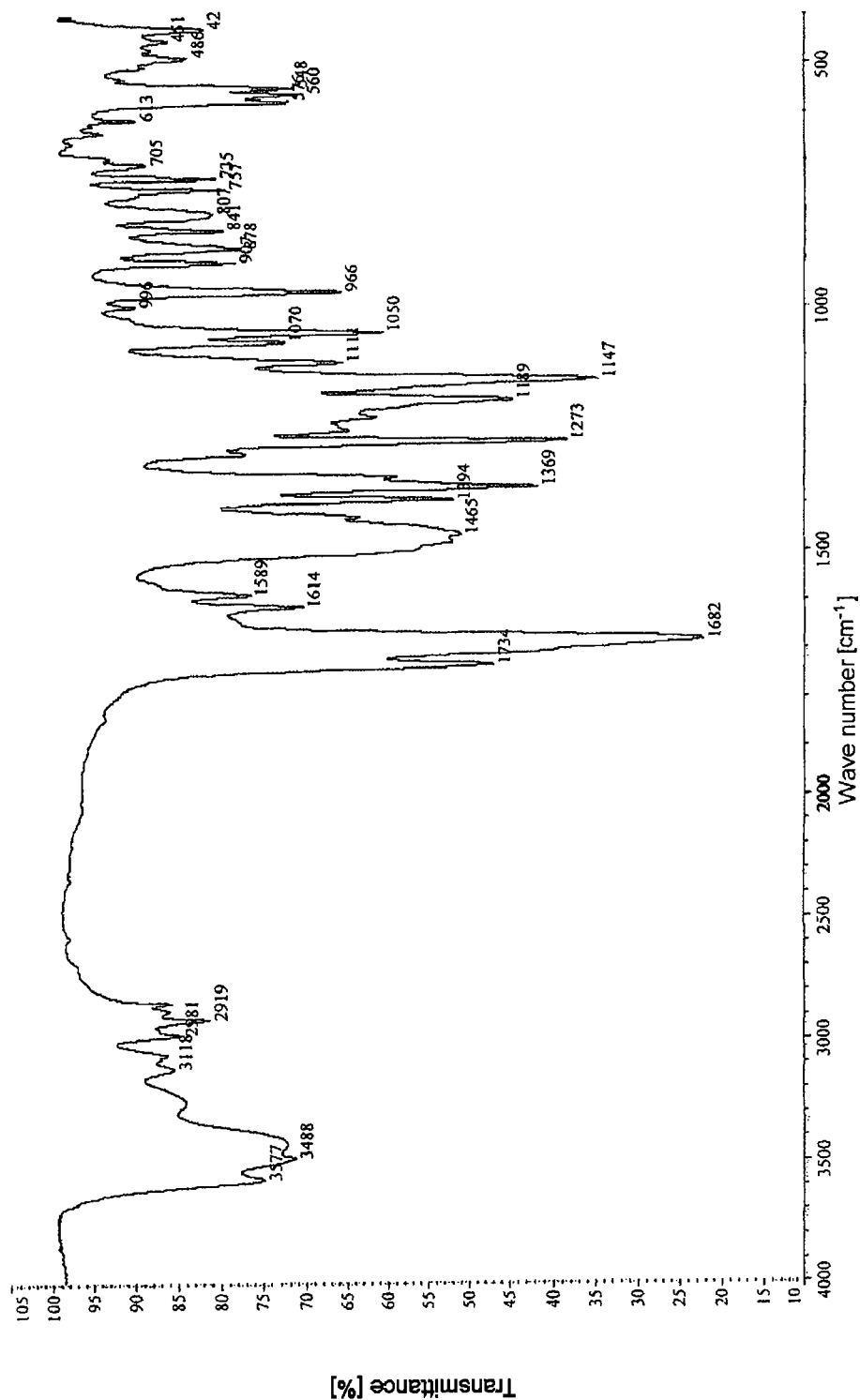
Figure 4:
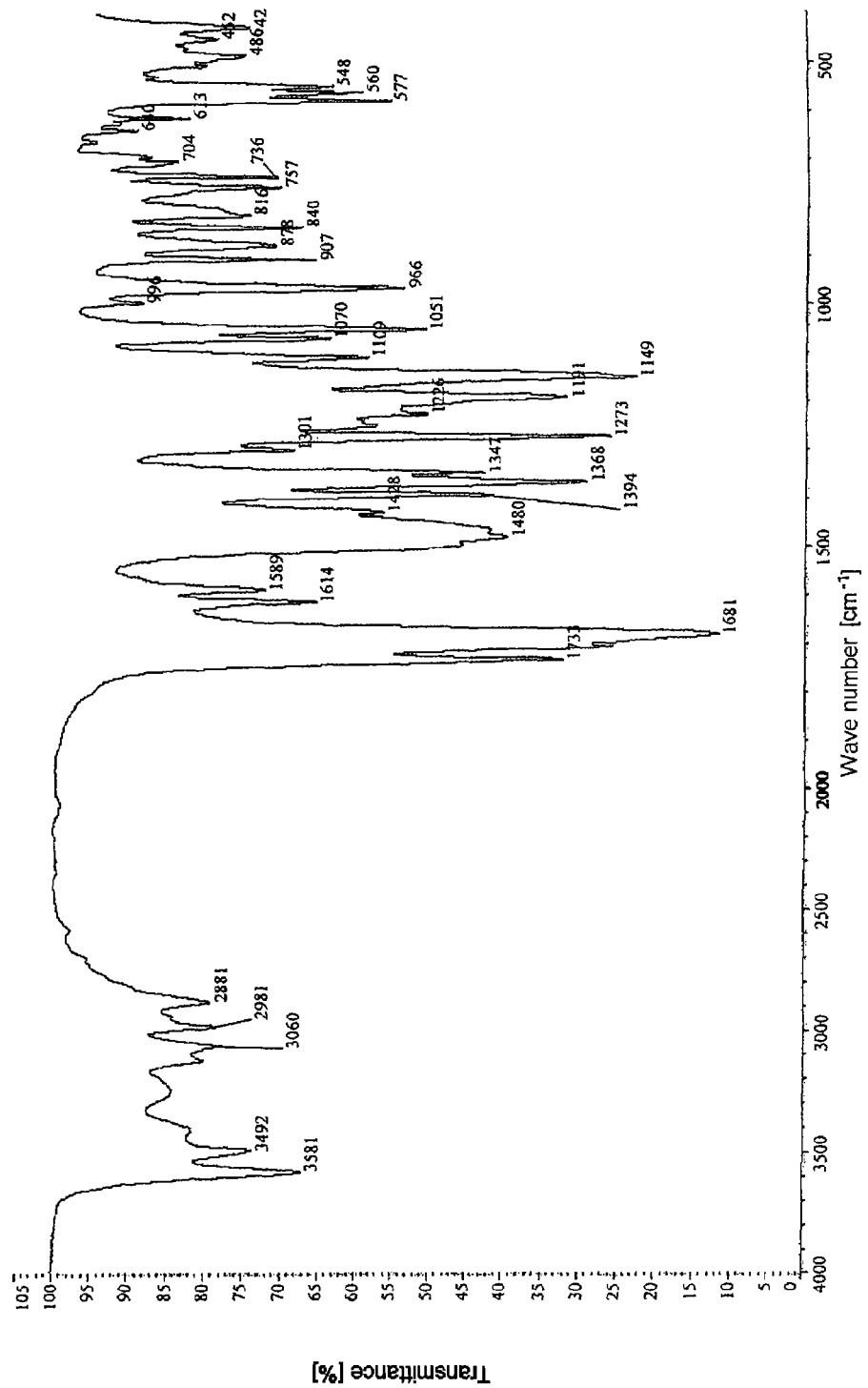

FIG. 3 shows the IR spectrum of form III, and FIG. 4 that of form IV. The IR spectra were recorded by means of FTIR spectrometers "Nicolet Magna 550" and "Nicolet Magna 750" from Thermo Electron Corp./USA in the wave number range of 400-4000 $cm^{-1}$ at a resolution of 4 $cm^{-1}$ (32 scans). The test specimens were KBr pellets.

The melting points and melting heats were determined via DSC using a Mettler Toledo DSC 25 apparatus from Mettler at a heating rate of 5 K/min in the range of from −5° C. to +180° C. The sample amount was 5 to 10 mg.

The crystallographic data of form III (Table 2) were determined using a single-crystal diffractometer from Bruker ("Bruker P4") using Cu—$K_\alpha$ radiation. The measurement was performed at −170° C.

EXAMPLE 1

Preparation of Form III of the Phenyluracil I by Crystallization of the Amorphous Form I from Tetrahydrofuran/Water Method a: 20 g of amorphous phenyluracil I were dissolved in 300 ml of THF. 300 ml of water were added in one portion to the solution at room temperature, followed by a further 300 ml of water after 48 hours. The resulting suspension was agitated for a further 3 days at room temperature. Thereafter, the resulting solid was filtered off from the mother liquor. The resulting crystalline material was analyzed by means of DSC and by means of X-ray powder diffractometry (XRD). Form III was obtained.

Method b: 20 g of amorphous phenyluracil I were dissolved in 300 ml of THF. The solution was heated to 40° C. and admixed with 300 ml of water in one portion. Thereafter, the mixture was cooled to room temperature, and the resulting solid was filtered off from the mother liquor. The resulting crystalline material was analyzed by means of DSC and by means of X-ray powder diffractometry (XRD). Form III was obtained.

EXAMPLE 2

Preparation of Form III of the Phenyluracil I by Crystallization of the Amorphous Form I from Acetone/Water 2 g of amorphous phenyluracil I were dissolved in 20 ml of acetone. The solution was heated to 40° C. and 5 portions water of 5 ml each were added in the course of 2 hours while maintaining the temperature. During this process, a precipitate started to crystallize out. The mixture was cooled slowly to room temperature (approximately 4 hours), and the resulting precipitate was filtered off. The presence of form III was confirmed by an X-ray powder diffractogram.

EXAMPLE 3

Preparation of Form III of the Phenyluracil I by Crystallization of the Amorphous Form I from Ethylene Glycol Monopropyl Ether/Water 2 g of amorphous phenyluracil I were dissolved in 20 ml of ethylene glycol monopropyl ether at 80° C. 25 ml of water were added thereto in the course of 1 hour while maintaining the temperature. During this process, a precipitate started to crystallize out. The mixture was cooled slowly to, and the resulting precipitate was filtered off. The presence of form III was confirmed by an X-ray powder diffractogram.

EXAMPLE 4

Preparation of Form IV of the Phenyluracil I by Crystallization of the Amorphous Form I from Isopropanol/Water 5 g of amorphous phenyluracil I were dissolved in 60 ml of isopropanol while heating at reflux. 50 ml of water were added thereto while maintaining the temperature. During this process, a precipitate started to crystallize out. The mixture was cooled to 50 to 60° C., the temperature was maintained for 2 days, whereupon the mixture was cooled to room temperature and the temperature was maintained for 2 days. Thereafter, the mixture was heated to 50 to 60° C., the temperature was maintained for 2 days, whereupon the mixture was cooled to room temperature and the resulting precipitate was filtered off. The resulting crystalline material was analyzed by means of DSC and by means of X-ray powder diffractometry (XRD). Form IV was obtained.

EXAMPLE 5

Preparation of Form IV of the Phenyluracil I by Reprecipitating the Amorphous Form I in Water 2 g of amorphous phenyluracil I were stirred in 20 ml of water for 2 days at room temperature. The solid was then removed by centrifugation. The presence of form IV was confirmed by an X-ray powder diffractogram.

EXAMPLE 6

Preparation of Form IV of the Phenyluracil I by Crystallization of the Amorphous Form I from Tetrahydrofuran/Water Method a: 20 g of amorphous phenyluracil I were dissolved in 300 ml of THF. 600 ml of water were added in one portion to the solution at room temperature. The resulting suspension was agitated for another 2 days at room temperature. Thereafter, the resulting solid was filtered off from the mother liquor. The presence of form IV was confirmed by an X-ray powder diffractogram.

EXAMPLE 7

Preparation of form III by reacting N-(2-chloro-4-fluoro-5-isocyanato-benzoyl)-N'-methyl(1-methyl-ethyl)sulfamide with ethyl 3-methylamino-4,4,4-trifluoro-crotonate, and precipitation from methanol/water 0.99 g (5.021 mmol) of ethyl 3-methylamino-4,4,4-trifluorocrotonate was stirred for 45 minutes in 25 ml of N,N- dimethylformamide and 50 ml of n-pentane under nitrogen under reflux conditions on a water separator. Thereafter, the n-pentane was distilled off until an internal temperature of 70° C. had been attained. The mixture was allowed to cool to 40° C., and 1.13 g (10.043 mmol) of potassium tert-butylate were then added in 3 portions with stirring in the course of 15 minutes at a temperature of up to 45° C., during which process a reddish-brown solution formed. After stirring for 20 minutes at 40° C., the mixture was allowed to cool, and 1.55 g (4.419 mmol) of N-(2-chloro-4-fluoro-5-isocyanatobenzoyl)-N'-methyl(1-methylethyl)sulfamide were then added in the course of 2 minutes at −15° C. to −10° C., during which process the substance dissolved instantly. The reaction mixture was stirred for 30 minutes at −10° C. and was then allowed to warm to 22° C., and stirring was continued for 30 minutes at this temperature.

The resulting reaction mixture was acidified with 0.46 g (12.553 mmol) of 4 n hydrochloric acid in 3.1 ml of dioxane with gentle cooling at 20-22° C., during which process a precipitate settled out, and the mixture was concentrated in vacuo. The resulting residue was partitioned in a solvent mixture of 100 ml of methyl tert-butyl ether and 100 ml of water. The organic phase was separated off and thereafter concentrated in vacuo to dryness. The glassy resin was taken up in an ice-cold mixture of methanol:water=7:3, with stirring, whereupon a precipitate started to form within 30 minutes. The residue was filtered off with suction and stirred for 0.5 hours in methyl tert-butyl ether at 0° C., filtered off with suction, washed with methyl tert-butyl ether and dried in vacuo, which gave 1.00 g (43.6% of theory) of the title compound as a colorless powder with a $^1$H NMR purity of 95% and a melting point of 107-122° C. The presence of form III was confirmed by X-ray powder diffractogram.

EXAMPLE 8

Preparation of Form III by Precipitation from Methyl Tert-Butyl Ether and Water of the Crude Product Generated in the Methylation 14.18 g (0.0274 mol) of 2-chloro-5-[3,6-dihydro-2,6-dioxo-4-(trifluoromethyl)-1-(2H)-pyrimidinyl]-4-fluoro-N-[[methyl(1-methylethyl)amino]sulfonyl]benzamide (93.9% pure) was added at 25° C. to a solvent mixture of 155 g of toluene and 31 g of tetrahydrofuran, and the mixture was then treated with a solution of 2.55 g (0.0319 mol) of sodium hydroxide (50% strength) in 61.2 g of water. The reaction mixture was treated with 0.88 g (0.0027 mol) of tetrabutylammonium bromide and 4.08 g (0.0329 mol) of dimethyl sulfate. The two-phase reaction mixture was stirred vigorously for 23 hours at 25° C. Thereafter, the aqueous phase was separated off, and the organic phase was washed twice within each case 100 ml of water. After drying the combined organic phase, the solvent was distilled off under reduced pressure, giving 15.4 g of a crude product which, according to quantitative HPLC, consisted of 77.6% of title compound (corresponds to a yield of 87.2%).

Thereupon, 14 g of the crude product obtained were added with stirring to a solvent mixture, heated at 40° C., of 60 ml of methyl tert-butyl ether and 6 ml of water. The mixture was allowed to cool slowly to 0° C., during which process a precipitate settled out. The precipitated solid was filtered off with suction and dried. This precipitation step gave 11.3 g of the title compound (purity determined by quantitative HPLC as the monohydrate: 93.3%; total yield after precipitation: 81.5%). The presence of form III was confirmed by an X-ray powder diffractogram.

EXAMPLE 9

Preparation of the Crystalline Hydrate Form III by Crystallization from Toluene/Water A solution of 0.92 mol of the 2-chloro-5-[3,6-dihydro-3-methyl-2,6-dioxo-4-trifluoro-methyl-1-(2H)-pyrimidinyl]-4-fluoro-N-[(methylisopropylamino)sulfonyl]benzamide in 95% toluene with 5% THF was treated with 180 g (10 mol) of water at 75° C. and cooled to 20° C. in the course of 3 hours. Stirring was continued for 15 hours, and the solid which had precipitated was filtered off at 20° C. The solid was washed with 150 g of toluene while still on the filter and dried in vacuo at temperatures <50° C. Yield: 0.82 mol. The presence of form III was confirmed by an X-ray powder diffractogram.

EXAMPLE 10

Preparation of the crystalline hydrate of 2-chloro-5-[3,6-dihydro-3-methyl-2,6-dioxo-4-trifluoromethyl-1-(2H)-pyrimidinyl]-4-fluoro-N-[(methylisopropylamino)-sulfonyl]benzamide (=form III) from the reaction solution 50.0 g (0.098 mol) of 2-chloro-5-[3,6-dihydro-2,6-dioxo-4-(trifluoromethyl)-1-(2H)-pyrimidinyl]-4-fluoro-N-{[methyl(1-methylethyl)amino]sulfonyl}benzamide, 3.2 g (0.0089 mol) of tetrabutylammonium bromide (=TBAB) and 15.1 g (0.12 mol) of dimethyl sulfate were introduced into the reaction vessel at 25° C. in a mixture of toluene, water and THF, and the mixture was heated to 40° C. Thereafter, a pH of 5.3-5.5 was established in the reaction mixture by addition of aqueous 10% strength NaOH solution. More aqueous 10% strength NaOH solution was added over the entire reaction period, so that, over the entire duration of the reaction, the pH was constantly the same as the pH which had been established previously. After the reaction had ended, stirring of the reaction mixture was continued for 3.5 hours at 40° C.

Method a): the phases were separated at 40° C. 250 g of water were added to the organic phase, and all of the toluene and the THF were removed by azeotropic distillation. The resulting mixture was treated with methanol at 65° C. and cooled to 20° C. in the course of 3 hours. This gave 45.6 g (82% of theory; purity 91.4%) of the phenyluracil as form III, which was identified on the basis of its X-ray powder diffractogram.

Method b): the phases were separated, and 65 to 70% of the solvent employed were distilled off. The solution was cooled to 75° C., and 18 g of water were subsequently added. The solution was cooled to 20° C. in a linear fashion in the course of 3 hours, and stirring was continued for 3 hours at 20° C. The precipitated solid was filtered off with suction and dried. This gave 44.8 g (83% of theory; purity 94.1%) of form III, which was identified on the basis of its X-ray powder diffractogram.

Like form I, forms III and IV are suitable as herbicide, but are superior to the former in terms of activity. The invention therefore also relates to plant protection compositions comprising the crystalline form III or form IV and adjuvants which are conventionally used in the formulation of plant protection compositions, in particular plant protection compositions in the form of aqueous or nonaqueous suspension concentrates. The invention also relates to a method of controlling undesired vegetation, which comprises allowing form III, or form IV, of the phenyluracil, preferably as a suitable active substance preparation, to act on plants, their environment and/or on seeds.

The herbicidal compositions comprising form III or form IV effect a very good control of vegetation on noncrop areas, especially at high application rates. In crops such as wheat, rice, maize, soya and cotton, they are active against broad-leaved weeds and grass weeds without inflicting substantial damage to the crop plants. This effect is particularly observed at low application rates.

Depending on the application method in question, form III or form IV, or the herbicidal compositions comprising it, can additionally be employed in a further number of crop plants to remove undesired plants. Crops which are suitable are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*)*, Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*)*, Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec.*, Manihot esculenta, Medicago sativa, Musa* spec.*, Nicotiana tabacum* (*N. rustica*)*, Olea europaea, Oryza sativa, Phaseolus lunatus, Phaseolus vulgaris, Picea abies, Pinus* spec.*, Pisum sativum, Prunus armeniaca, Prunus avium, Prunus cerasus, Prunus dulcis, Prunus domesticua, Prunus persica, Pyrus communis, Ribes sylvestre, Ricinus communis, Saccharum officinarum, Secale cereale, Solanum tuberosum, Sorghum bicolor* (*s. vulgare*)*, Theobroma cacao, Trifolium pratense, Triticum aestivum, Triticum durum, Vicia faba, Vitis vinifera* and *Zea mays*.

In addition, form III or form IV, or the herbicidal compositions comprising it, can also be used in crops which tolerate the effect of herbicides as the result of breeding, including genetic engineering methods.

Furthermore, form III or form IV, or the herbicidal compositions comprising it, can also be used in crops which tolerate attack by insects or fungi as the result of breeding, including genetic engineering methods.

Moreover, it has been found that forms III and IV are also suitable for the defoliation and desiccation of plant parts, for which crops plants such as cotton, potato, oilseed rape, sunflower, soybean or field beans, in particular cotton, are suitable. In this regard, there have been found compositions for the desiccation and/or defoliation of plants, processes for the preparation of these compositions and methods of desiccating and/or defoliating plants using form III or form IV.

As desiccants, forms III and IV are particularly suitable for desiccating the aerial parts of crop plants such as potato, oilseed rape, sunflower and soybean. This makes possible the fully mechanical harvesting of these important crop plants. Also of economic interest is to facilitate harvesting, which is made possible by concentrating within a certain period of time the dehiscence, or reduction of adhesion to the tree, in citrus fruit, olives or other species and varieties of pome fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval within which the individual cotton plants mature leads to an increased fiber quality after harvesting.

Moreover, it has been found that forms III and IV are also suitable for the control of conifers, in particular of conifer seedlings which grow naturally, specifically for the control of pine seedlings which grow naturally.

Forms III and IV are also suitable for the control of weeds in crop plants such as, for example, soybean, cotton, oilseed rape, flax, lentils, rice, sugar beet, sunflower, tobacco and cereals, such as, for example maize or wheat.

Form III or IV or the herbicidal compositions comprising it can be applied, for example in the form of directly sprayable aqueous solutions, powders, suspensions, also highly concentrated aqueous, oily or other suspensions, oil suspensions, pastes, dusts, tracking powders or granules, by means of spraying, atomizing, dusting, tracking or drenching. The use forms depend on the intended purposes; in any case, this should ensure the finest possible distribution of the active substances according to the invention.

The herbicidal compositions comprise a herbicidally active amount of form III or IV and auxiliaries and carriers conventionally used for the formulation of plant protection products.

Carriers which are suitable are, in principle, all solid substances which are conventionally employed in plant protection products, in particular in herbicides.

Examples of solid carriers are mineral earths such as silica gels, silicates, talc, kaolin, attaclay, limestone, lime, chalk, boll, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and products of vegetable origin such as cereal meal, tree bark meal, wood meal and nutshell meal, cellulose powders and other solid carriers.

In the case of liquid formulations of form III or IV, the compositions have a liquid phase. Suitable as the liquid phase are, in principle, water and those organic solvents in which the forms III or IV are not soluble or only sparingly soluble, for example those in which the solubility of forms III or IV of the phenyluracil I at 25° C. and 1013 mbar is not more than 1% by weight, in particular not more than 0.1% by weight and specifically not more than 0.01% by weight.

Preferred liquid phases are, in particular, water and aqueous solvents, i.e. solvent mixtures which, besides water, also comprise up to 30% by weight, but preferably not more than 10% by weight, based on the total amount of water and solvent, of one or more water-miscible organic solvents, for example water-miscible ethers such as tetrahydrofuran, methyl glycol, methyl diglycol, alkanols such as methanol, ethanol, isopropanol, or polyols such as glycol, glycerol, diethylene glycol, propylene glycol and the like.

Preferred liquid phases are, furthermore, nonaqueous organic solvents in which the solubility of form III or IV of the phenyluracil I at 25° C. and 1013 mbar is not more than 1% by weight, in particular not more than 0.1% by weight and specifically not more than 0.01% by weight. These include, in particular, aliphatic and cycloaliphatic hydrocarbons and oils, in particular those of vegetable origin, furthermore $C_1$-$C_4$-alkyl esters of saturated or unsaturated fatty acids or fatty acid mixtures, in particular the methyl esters, for example methyl oleate, methyl stearate, rapeseed oil methyl esters, but also paraffinic mineral oils and the like.

Typical auxiliaries comprise surface-active substances, in particular the wetters and dispersants/dispersion aids which are conventionally employed in plant protection compositions, furthermore additives which modify the viscosity (thickeners), antifoam agents, antifreeze agents, pH regulators, stabilizers, anticaking agents and biocides (preservatives).

The invention relates in particular to compositions for plant protection in the form of an aqueous suspension concentrate (SC). Such suspension concentrates comprise form III or IV of the phenyluracil I in a finely divided particulate form, where the particles of form III or IV are suspended in an aqueous phase. The size of the active substance particles, i.e. the size not exceeded by 90% by weight of the active substance particles, is typically below 30 µm, in particular below 20 µm. Advantageously, at least 40% by weight and in particular at least 60% by weight of the particles in the SCs according to the invention have diameters of below 2 µm.

Besides the active substance, aqueous suspension concentrates typically comprise surface-active substances and, if appropriate, antifoam agents, thickeners, antifreeze agents, stabilizers (biocides), pH regulators and anticaking agents.

The amount of active substance, i.e. the total amount of phenyluracil of the form III or IV and, if appropriate, further active substances in such SCs are usually in the range of from 10 to 70% by weight, in particular in the range of from 20 to 50% by weight, based on the total weight of the suspension concentrate.

Suitable surface-active substances are, preferably, anionic and nonionic surfactants. Other suitable surface-active substances are protective colloids. As a rule, the amount of surface-active substances will amount to from 0.5 to 30% by weight, in particular 1 to 20% by weight, based on the total weight of the aqueous SCs according to the invention. Preferably, the surface-active substances comprise at least one anionic surface-active substance and at least one nonionic surface-active substance, the weight ratio of anionic to nonionic surface-active substance being typically in the range of from 10:1 to 1:10.

Examples of anionic surface-active substances (surfactants) include alkylaryl-sulfonates, phenylsulfonates, alkyl sulfates, alkylsulfonates, alkyl ether sulfates, alkylaryl ether sulfates, alkyl polyglycol ether phosphates, polyarylphenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and condensates of phenolsulfonic acid, formaldehyde and urea, lignin-sulfite waste liquor and lignosulfonates, alkyl phosphates, alkylaryl phosphates, for example tristyryl phosphates, and also polycarboxylates such as, for example, polyacrylates, maleic anhydride/olefin copolymers (for example Sokalan® CP9, BASF), including the alkali metal, alkaline-earth metal, ammonium and amine salts of the abovementioned substances. Preferred anionic surface-active substances are those which contain at least one sulfonate group and in particular their alkali metal salts and their ammonium salts.

Examples of nonionic surface-active substances comprise alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and their mixtures. Preferred nonionic surface-active substances are fatty alcohol ethoxylates, alkyl polyglycosides, glycerol fatty acid esters, castor oil alkoxylates, fatty acid alkoxylates, fatty acid amide alkoxylates, lanolin ethoxylates, fatty acid polyglycol esters and ethylene oxide/propylene oxide block copolymers, and mixtures of these.

Protective colloids are, typically, water-soluble amphiphilic polymers. Examples are proteins and denatured proteins such as casein, polysaccharides such as water-soluble starch derivatives and cellulose derivatives, in particular hydrophobically modified starches and celluloses, furthermore polycarboxylates such as polyacrylic acid and acrylic acid copolymers, polyvinyl alcohol, polyvinyl pyrrolidone, vinylpyrrolidone copolymers, polyvinylamines, polyethyleneimines, and polyalkylene ethers.

Viscosity-modifying additives (thickeners) which are suitable for the aqueous SCs according to the invention are, in particular, compounds which impart a modified flowing behavior to the formulation, for example a high viscosity in the static state and low viscosity in the state of motion. Suitable compounds are, in principle, all those employed in suspension concentrates for this purpose. Substances to be mentioned are, for example, inorganic substances, for example layer silicates and organic modified layer silicates such as bentonites or attapulgites (for example Attaclay® from Engelhardt), and organic substances such as polysaccharides and heteropolysaccharides such as Xanthan Gum® (Kelzan® from Kelco), Rhodopol® 23 (Rhone Poulenc) or Veegum® (from R. T. Vanderbilt), with Xanthan-Gum® being used by preference. The amount of the viscosity-modifying additives is frequently 0.1 to 5% by weight, based on the total weight of the SCs.

Antifoam agents which are suitable for the aqueous SCs according to the invention are, for example, silicone emulsions which are known for this purpose (Silikon® SRE, from Wacker or Rhodorsil® from Rhodia), long-chain alcohols, fatty acids and their salts, antifoams of the aqueous wax dispersion type, solid antifoams (known as Compounds), organofluorine compounds and mixtures of these. The amount of antifoam agents is typically 0.1 to 1% by weight, based on the total weight of the SCs.

Preservatives may also be added to the suspension concentrates according to the invention for the purposes of stabilizing them. Suitable preservatives are those based on isothiazolones, for example Proxel® from ICI or Acticide® RS from Thor Chemie or Kathon® MK from Rohm & Haas. The amount of preservative is typically 0.05 to 0.5% by weight, based on the total weight of the SCs.

Suitable antifreeze agents are liquid polyols, for example ethylene glycol, propylene glycol or glycerol, and also urea. The amount of antifreeze agents is, as a rule, 1 to 20% by weight, in particular 5 to 10% by weight, based on the total weight of the aqueous suspension concentrate.

If appropriate, the aqueous SCs according to the invention may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

If the formulations of form III or IV are employed for the treatment of seed, they may comprise further customary constituents as are employed in seed treatment, for example seed dressing or coating. Besides the abovementioned constituents, these include in particular colorants, adhesives, fillers and plasticizers.

Colorants which are suitable are all dyes and pigments conventionally used for such purposes. Both pigments, which are sparingly soluble in water, and dyes, which are water-soluble, may be used. Examples which may be mentioned are the dyes and pigments known under the names Rhodamin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorant will usually not exceed 20% by weight of the formulation and is preferably in the range of from 0.1 to 15% by weight, based on the total weight of the formulation.

Stickers which are suitable are all customary binders which can be employed in seed-dressing products. Examples of suitable binders comprise thermoplastic polymers such as polyvinylpyrrolidone, polyvinyl acetate, polyvinyl alcohol and tylose, furthermore polyacrylates, polymethacrylates, polybutenes, polyisobutenes, polystyrene, polyethyleneamines, polyethylene amides, the abovementioned protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropylcellulose and starch derivatives and modified starches, dextrins, maltodextrins, alginates and chitosans, furthermore fats, oils, proteins, including casein, gelatin and zein, gum arabic, shellac. Preferably, the stickers are tolerated by plants, i.e. they have no, or no substantial, phytotoxic effects. The stickers are preferably biodegradable. The sticker is preferably selected so that it acts as the matrix for the active components of the formulation. The amount of sticker will usually not exceed 40% by weight of the formulation and is preferably in the range of from 1 to 40% by weight and in particular in the range of from 5 to 30% by weight, based on the total weight of the formulation.

Besides the sticker, the seed treatment formulation may also comprise inert fillers. Examples are the abovementioned solid carriers, in particular finely divided inorganic materials such as clays, chalk, bentonite, kaolin, talc, perlite, mica, silica gel, diatomaceous earth, quartz powder, montmorillonite, but also finely divided organic materials such as wood meal, cereal meal, active charcoal and the like. The amount of filler will preferably be selected so that the total amount of filler does not exceed 75% by weight based on the total weight of all nonvolatile components of the formulation. Frequently, the amount of filler will be in the range of from 1 to 50% by weight, based on the total weight of all nonvolatile components of the formulation.

In addition, the seed treatment formulation may also comprise a plasticizer which increases the flexibility of the coating. Examples of plasticizers are oligomeric polyalkylene glycols, glycerol, dialkyl phthalates, alkyl benzyl phthalates, glycol benzoates and comparable compounds. The amount of plasticizer in the coating is frequently in the range of from 0.1 to 20%, based on the total weight of all nonvolatile components of the formulation.

In particular, the invention also relates to plant protection compositions in the form of a nonaqueous suspension concentrate. Such suspension concentrates comprise form III, or form IV, of the phenyluracil I in a finely divided particulate form, the particles of form III, or IV, being suspended in a nonaqueous phase. The size of the active substance particles, i.e. the size which is not exceeded by 90% by weight of the active substance particles, is typically below 30 µm, in particular below 20 µm. Advantageously, at least 40% by weight and in particular at least 60% by weight of the particles in the nonaqueous SCs have diameters of below 2 µm.

Besides the active substance, non-aqueous suspension concentrates typically comprise surface-active substances and, if appropriate, antifoam agents, thickeners, antifreeze agents, stabilizers (biocides), pH regulators and anticaking agents.

The amount of active substance, i.e. the total amount of phenyluracil in the form III or IV and, if appropriate, further active substances, in the non-aqueous SCs is usually in the range of from 10 to 70% by weight, in particular in the range of from 20 to 50% by weight, based on the total weight of the non-aqueous suspension concentrate.

Suitable surface-active substances are, preferably, the abovementioned anionic and nonionic surfactants. As a rule, the amount of surface-active substances will amount to from 1 to 30% by weight, in particular 2 to 20% by weight, based on the total weight of the aqueous SCs according to the invention. Preferably, the surface-active substances comprise at least one anionic surface-active substance and at least one nonionic surface-active substance, the weight ratio of anionic to nonionic surface-active substance being typically in the range of from 10:1 to 1:10.

The forms III and IV according to the invention may also be formulated as powders, including tracking powders, and dust. Such formulations can be prepared by mixing or concomitantly grinding the form III, or IV, with a solid carrier and, if appropriate, further auxiliaries.

Forms III and IV according to the invention may also be formulated as granules, for example coated granules, impregnated granules and homogeneous granules. Such formulations can be prepared by binding the active substances to solid carriers. Solid carriers are mineral earths such as silicas, silica gels, silicates, talc, kaolin, limestone, lime, chalk, boll, loess, clay, dolomite, diatomaceous earth, calcium sulfate, magnesium sulfate, magnesium oxide, ground synthetic substances, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of form III, or IV, in the ready-to-use preparations can be varied within wide limits. In general, the formulations comprise approximately from 11 to 98% by weight, preferably from 10 to 95% by weight, based on the total weight of active substances.

The formulation examples which follow illustrate how such preparations are made:

I. 20 parts by weight of form III, or IV, are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. This gives a water-dispersible powder which comprises the form III, or IV. Finely distributing the mixture in 20 000 parts by weight of water gives a spray mixture which comprises 0.1% by weight of form III, or IV.

II. 3 parts by weight of form III, or IV, are mixed with 97 parts by weight of finely divided kaolin. This gives a dust which comprises 3% by weight of form III, or IV.

III. 20 parts by weight of form III, or IV I, are mixed intimately with 2 parts by weight of calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil. This gives a stable nonaqueous suspension concentrate of the form III, or IV.

IV. 10 parts by weight of form III, or IV, were formulated as suspension concentrate in a solution of 17 parts by weight of a poly(ethylene glycol)(propylene glycol) block copolymer, 2 parts by weight of a phenolsulfonic acid/formaldehyde condensate and approximately 1 part by weight of other auxiliaries (thickeners, antifoams) in a mixture of 7 parts by weight of propylene glycol and 63 parts by weight of water.

V. 30.5 parts by weight of form III, or IV, were formulated as suspension concentrate in a solution of 1 part by weight of a poly(ethylene glycol)(propylene glycol) block copolymer, 1 part by weight of a phenolsulfonic acid/formaldehyde condensate and approximately 1 part by weight of other auxiliaries (thickeners, antifoams) in a mixture of 6 parts by weight of propylene glycol and 61 parts by weight of water.

The application of form III, or IV, or of the herbicidal compositions comprising it is accomplished in the form of aqueous spray mixtures, unless the formulation is ready to use. These aqueous spray mixtures are prepared by dilution with water of the abovementioned formulations which comprise form III, or IV, of the phenyluracil I. The spray mixtures may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and nonphytotoxic oils or oil concentrates. As a rule, these constituents are added to the spray mixture before, during or after dilution of the formulations according to the invention.

Form III, or IV, or other herbicidal compositions comprising it can be applied by the pre-emergence or the post-emergence method. If the phenyluracil I is less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Depending on the aim of the control measures, the season, the target plants and the growth stage, the application rates of form III, or IV, are from 0.001 to 3.0, preferably from 0.01 to 1.0 kg/ha active substance (a.s.).

To widen the spectrum of action and to obtain synergistic effects or to increase the selectivity, the forms III and IV can be mixed with a large number of representatives of other groups of herbicidal or growth-regulatory active substances or with safeners and applied together with these. The forms III and IV can, for example, be employed, and/or applied, analogously to the mixtures of phenyluracils I with herbicides, growth regulators and/or safeners, which mixtures have been described in WO 2003/024221, WO 2004/080183, WO 2006/097509 and WO 2007/042447. Examples of suitable mixing partners are 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzyl-isoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic acid esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils. Examples of suitable safeners are (quinolin-8-oxy)acetic acids, 1-phenyl-5-haloalkyl-1H-1,2,4-triazole-3-carboxylic acids, 1-phenyl-4,5-dihydro-5-alkyl-1H-pyrazole-3,5-di-dicarboxylic acids, 4,5-dihydro-5,5-diaryl-3-isoxazolecarboxylic acids, dichloroacetamides, alpha-oximinophenylacetonitriles, acetophenone oximes, 4,6-dihalo-2-phenylpyrimidines, N-[[4-(aminocarbonyl)phenyl]sulfonyl]-2-benzamides, 1,8-naphthalic anhydride, 2-halo-4-(haloalkyl)-5-thiazolecarboxylic acids, phosphorothiolates and N-alkyl-O-phenyl carbamates and their agriculturally useful salts, and with the proviso that they have an acid function, their agriculturally useful derivatives, such as amides, esters and thioesters.

Moreover, it may be useful to apply the form III, or IV, alone or in combination with other herbicides and/or safeners, jointly as a mixture with yet further plant protection agents, for example with agents for controlling pests or phytopathogenic fungi or bacteria. Also of interest is the miscibility with mineral salt solutions which are employed for alleviating nutritional and trace element deficiencies. Nonphytotoxic oils and oil concentrates may also be added.

The herbicidal activity of forms III and IV was demonstrated by the following greenhouse experiments:

The culture containers used were plastic pots which were filled with soil (for example loamy sand with approximately 3.0% humus) as the substrate. The seeds of the test plants were sown separately for each species.

In the case of the pre-emergence treatment, the active substances, which were suspended in water, were applied directly after sowing, by means of finely distributing nozzles. The containers were irrigated gently to promote germination and growth and subsequently covered with translucent plastic tents until the plants had rooted. This covering brings about a uniform germination of the test plants, unless this has been adversely affected by the active substances.

For the purposes of the post-emergence treatment, the test plants were first grown to a height of 3 to 15 cm, depending on the growth form, and only then treated with the active substances which have been suspended in water. To this end, the test plants were either sown directly and grown in the same containers, or they were first grown separately as seedlings and transplanted into the test containers a few days prior to the treatment.

The plants were kept at temperatures of from 10 to 25° C., or 20 to 35° C., respectively, depending on the species. The test period extended over 2 to 4 weeks. During this period, the plants were tended, and their response to the individual treatments was evaluated.

The evaluation was carried out using a scale of from 0 to 100. 100 means no emergence of the plants, or complete destruction of at least the aerial parts, and 0 means no damage or normal course of growth.

The abovementioned methods were used to compare, in a greenhouse test, forms III and IV according to the invention and, as comparison compound, form I, which is disclosed in WO 01/83459, in each case formulated as aqueous suspension concentrate (SC; 100 g/l), if appropriate with the addition of 1 l/ha Rustica ÖI®. The suspension concentrates had the following composition:

| | |
|---|---|
| phenyluracil I | 100 g/l |
| 1,2-propylene glycol | 70 g/l |
| dispersant I | 167 g/l |
| dispersant II | 20 g/l |
| xanthan gum | 3 g/l |
| biocide | 1.8 g/l |
| water | to 1 l | dispersant I: EO/PO block copolymer
dispersant II: phenolsulfonic acid/formaldehyde condensate The plants used in the greenhouse experiments belong to the following species:

| Scientific name | English name |
|---|---|
| Amaranthus retroflexus | redroot pigweed |
| Ambrosia elatior | common ragweed |
| Capsella bursa-pastoris | shepherdspurse |
| Chenopodium album | common lambsquarters |
| Euphorbia heterophylla | spurge |
| Galium aparine | catchweed bedstraw |
| Glycine max | soybean |
| Helianthus annuus | sunflower |
| Hordeum vulgare | spring or winter barley |
| Kochia scoparia | fireweed |
| Matricaria inodora | scentless mayweed |
| Mercurialis annua | annual mercury |
| Polygonum convolvulus | wild buckwheat |
| Salsola kali ssp. ruthenica | russian thistle |
| Secale cereale | winter rye |
| Sinapis arvensis | wild mustard |
| Sonchus arvensis | field sowthistle |
| Stellaria media | chickweed |
| Thlaspi arvense | frenchweed |
| Triticum aestivum | spring wheat |
| Veronica hederaefolia | ivyleaf speedwell |
| Veronica persicaria | birdseye speedwell |
| Viola arvensis | field violet |

TABLE 4

Comparison of the herbicidal activity of form III with form I, which is disclosed in WO 01/83459, when applied pre-emergence (greenhouse)

| | | Active substance | |
|---|---|---|---|
| Test plants | Application rate (g/ha a.s.) | Form III | Modification I |
| | | Damage [%] | |
| Useful plant: | | | |
| Glycine max | 25 | 30 | 70 |
| | 12.5 | 20 | 30 |
| Harmful plant: | | | |
| Stellaria media | 12.5 | 70 | 65 |
| Ambrosia elatior | 12.5 | 80 | 60 |
| Helianthus annuus | 12.5 | 75 | 70 |
| Euphorbia heterophylla | 12.5 | 100 | 95 |
| | 6.25 | 90 | 40 |
| Mercurialis annua | 6.25 | 65 | 40 |

TABLE 5

Comparison of the herbicidal activity of form III with form I, which is disclosed in WO 01/83459, when applied post-emergence, with addition of 1 l/ha Rustica ÖI ® (greenhouse)

| | | Active substance | |
|---|---|---|---|
| Test plants | Application rate (g/ha a.s.) | Form III | Form I |
| | | Damage [%] | |
| Useful plant: | | | |
| Hordeum vulgare (spring barley) | 20 | 5 | 15 |
| Hordeum vulgare (winter barley) | 20 | 5 | 20 |
| | 15 | 5 | 15 |
| Secale cereale | 20 | 5 | 15 |
| | 15 | 0 | 10 |
| | 10 | 0 | 10 |
| Triticum aestivum | 20 | 10 | 15 |
| Harmful plant: | | | |
| Chenopodium album | 15 | 80 | 70 |
| Galium aparine | 15 | 100 | 75 |
| Matricaria inodora | 5 | 100 | 65 |
| Polygonum convolvulus | 15 | 100 | 70 |
| Veronica hederaefolia | 15 | 70 | 50 |
| Veronica persicaria | 15 | 100 | 70 |
| Viola arvensis | 5 | 100 | 40 |

TABLE 6

Comparison of the herbicidal activity of form III with form I, which is disclosed in WO 01/83459, when applied post-emergence (greenhouse)

| | | Active substance | |
|---|---|---|---|
| Test plants | Application rate (g/ha a.s.) | Form III | Form I |
| | | Damage [%] | |
| Useful plant: | | | |
| Hordeum vulgare (winter barley) | 15 | 0 | 5 |
| Secale cereale | 20 | 5 | 15 |
| Triticum aestivum | 20 | 5 | 10 |
| Harmful plant: | | | |
| Amaranthus retroflexus | 10 | 100 | 40 |
| Capsella bursa-pastoris | 15 | 70 | 20 |
| Kochia scoparia | 20 | 100 | 45 |
| Matricaria inodora | 15 | 100 | 65 |
| Salsola kali ssp. ruthenica | 20 | 100 | 80 |
| Sinapis arvensis | 10 | 60 | 50 |
| Sonchus arvensis | 15 | 100 | 60 |
| Thlaspi arvense | 10 | 100 | 30 |
| Veronica persicaria | 15 | 100 | 40 |
| Viola arvensis | 15 | 100 | 40 |

The test results show clearly that form III according to the invention has an improved tolerance by the crop plant in comparison with form I, which is known, while simultaneously exhibiting a markedly improved herbicidal activity.

We claim:

1. A crystalline hydrate of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide, which is selected from the group consisting of the hydrate (a) which in an X-ray powder diffractogram at 25° C. and Cu—$K_\alpha$ radiation, shows at least one reflex at the 2θ value of 11.6±0.2° and additionally at least five of the following reflexes, given as 2θ values: 5.1±0.2°, 10.1±0.2°, 10.8±0.2°, 13.9±0.2°, 15.1±0.2°, 16.1±0.2°, 17.9±0.2°, 20.2±0.2°, 24.5±0.2°, and the hydrate (b), which in an X-ray powder diffractogram at 25° C. and Cu—$K_\alpha$ radiation, shows at least one reflex at the 2θ value of 12.1±0.2° and additionally at least five of the following reflexes, given as 2θ values: 5.2±0.2°, 10.2±0.2°, 10.9±0.2°, 14.0±0.2°, 14.6±0.2°, 15.3±0.2°, 19.2+0.2°, 19.9±0.2°, 20.5±0.2°, 24.7±0.2°, 26.7±0.2°, 27.8±0.2°.

2. The hydrate according to claim 1, comprising 0.8 to 1.2 mol of water, per mole of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide.

3. The hydrate according to claim 1, with a melting peak in the range of from 100 to 140° C.

4. The hydrate according to claim 1, with a 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide content of at least 94% by weight, based on the total amount of the organic constituents in the hydrate.

5. 2-Chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide, consisting essentially of hydrate (a) according to claim 1.

6. 2-Chloro-5-[3,6-dihydro-3-methyl-2,6-dioxo-4-(trifluoromethyl)-1-(2H)-pyrimidinyl]-4-fluoro-N-[[methyl(1-methylethyl)amino]sulfonyl]benzamide, consisting essentially of hydrate (b) according to claim 1.

7. A process for the preparation of a hydrate according to claim 1, comprising the crystallization of a solution of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in an organic solvent in the presence of water.

8. A process for the preparation of a hydrate according to claim 1, comprising the suspending of amorphous 2-chloro-5-[3,6-dihydro-3-methyl-2,6-dioxo-4-(trifluoromethyl)-1-(2H)pyrimidinyl]-4-fluoro-N-[[methyl(1-methyl-ethyl)amino]sulfonyl]benzamide in water or a water-containing organic solvent.

9. A plant protection composition comprising a hydrate according to claim 1 and auxiliaries conventionally employed for the formulation of plant protection compositions.

10. The plant protection composition according to claim 9 in the form of an aqueous suspension concentrate.

11. The plant protection composition according to claim 9 in the form of a nonaqueous suspension concentrate.

12. The plant protection composition according to claim 9 in the form of a water-dispersible powder or water-dispersible granules.

13. A method of controlling undesired vegetation, wherein a hydrate of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide according to claim 1 is allowed to act on plants, their environment and/or on seeds.

14. The method of claim 13, wherein the hydrate comprises 0.8 to 1.2 mol of water, per mole of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide.

15. The method of claim 13, wherein the hydrate has a melting peak in the range of from 100 to 140° C.

* * * * *

UNITED STATES PATENT AND TRADEMARK OFFICE
CERTIFICATE OF CORRECTION

PATENT NO. : 8,357,695 B2
APPLICATION NO. : 12/444651
DATED : January 22, 2013
INVENTOR(S) : Schmidt et al.

It is certified that error appears in the above-identified patent and that said Letters Patent is hereby corrected as shown below:

On the Title Page, (75) Inventors, the residence address of Gerhard Cox should be changed from "Dükheiim" to --Dürkheim--.

Signed and Sealed this
Second Day of April, 2013

Teresa Stanek Rea
*Acting Director of the United States Patent and Trademark Office*